United States Patent
Turner

(10) Patent No.: US 9,387,218 B2
(45) Date of Patent: Jul. 12, 2016

(54) COMPOSITION FOR THE TREATMENT OF INFLAMMATORY AND IMMUNE DISORDERS

(71) Applicant: EAGLEPHARMA PTY LTD, Buderim, Queensland (AU)

(72) Inventor: Paul Frederick Turner, Buderim (AU)

(73) Assignee: EAGLEPHARMA PTY LTD, Buderim, Queensland (AU)

(*) Notice: Subject to any disclaimer, the term of this patent is extended or adjusted under 35 U.S.C. 154(b) by 0 days.

(21) Appl. No.: 14/390,184

(22) PCT Filed: Apr. 2, 2013

(86) PCT No.: PCT/GB2013/050865
§ 371 (c)(1),
(2) Date: Oct. 2, 2014

(87) PCT Pub. No.: WO2013/150292
PCT Pub. Date: Oct. 10, 2013

(65) Prior Publication Data
US 2015/0111850 A1    Apr. 23, 2015

(30) Foreign Application Priority Data

Apr. 2, 2012  (AU) ................. 2012901301

(51) Int. Cl.
*A61K 31/10* (2006.01)
*A61K 31/198* (2006.01)
*A61K 31/465* (2006.01)
*A61K 31/7008* (2006.01)
*A61K 31/455* (2006.01)

(52) U.S. Cl.
CPC ............ *A61K 31/7008* (2013.01); *A61K 31/10* (2013.01); *A61K 31/198* (2013.01); *A61K 31/455* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 2003/0118672 A1* | 6/2003 | McPeak | A61K 31/10 424/750 |
| 2003/0185904 A1* | 10/2003 | Reynolds | A61K 31/7008 424/702 |
| 2006/0029647 A1 | 2/2006 | Friesen et al. | |
| 2006/0251750 A1* | 11/2006 | Tabor | A61K 31/4188 424/757 |
| 2007/0020218 A1* | 1/2007 | Richardson | A61K 31/198 424/70.13 |
| 2007/0218042 A1 | 9/2007 | Khaled | |
| 2009/0110674 A1* | 4/2009 | Loizou | A61K 36/00 424/94.2 |

FOREIGN PATENT DOCUMENTS

EP    0 103 836 B1    1/1991
WO    2012/045118 A1    4/2012

OTHER PUBLICATIONS

Barrager et al., *The Journal of Alternative and Complementary Medicine*, 8(2): 167-173 (2002).
Kim et al., *Biol. Pharm. Bull.*, 32(4): 651-656 (2009).
Largo et al., *OsteoArthritis and Cartilage*, 11: 290-298 (2003).
Spittler et al., *Faseb J.*, 13: 563-571 (1999).
Usha et al., *Clin. Drug. Invest.*, 24(6): 353-363 (2004).
Wheeler et al., *CMLS Cell. Mol. Life Sci.*, 56: 843-856 (1999).
European Patent Office, International Search Report in International Patent Application PCT/GB2013/050865 (May 28, 2013).

* cited by examiner

*Primary Examiner* — Layla Berry
(74) *Attorney, Agent, or Firm* — Leydig, Voit & Mayer, Ltd.

(57) ABSTRACT

The invention relates to the treatment of an inflammatory or immune disorder with a pharmaceutical composition including methylsulphonylmethane, glucosamine and glycine or pharmaceutically acceptable salts or derivatives of these compounds.

14 Claims, No Drawings

COMPOSITION FOR THE TREATMENT OF INFLAMMATORY AND IMMUNE DISORDERS

CROSS-REFERENCE TO RELATED APPLICATIONS

This patent application is the U.S. national stage of PCT/GB2013/050865, filed Apr. 2, 2013, which claims the benefit of Australian Patent Application No. AU2012901301, filed Apr. 2, 2012, which are incorporated herein by reference in their entireties.

FIELD OF THE INVENTION

The present invention relates to the treatment of inflammatory and immune disorders using a composition including methylsulphonylmethane (MSM), glucosamine and glycine or pharmaceutically acceptable salts or derivatives of these compounds.

BACKGROUND OF THE INVENTION

A large number of diseases and disorders are associated with a dysfunctional immune response leading to inflammation and other clinical manifestations and pathology. It has been long established that certain disorders, such as allergies, including allergic reaction to insect bites and allergic rhinitis, skin disorders, such as psoriasis, seborrheic dermatitis, seborrheic keratosis, atopic dermatitis, acne vulgaris; solar keratosis, Crohn's disease and rheumatoid arthritis are associated with an inflammatory response. However, recent studies suggest that a greater variety of diseases and disorders have inflammatory response-based symptoms. These include such a diversity of disorder as major depression, cerebral palsy, Bell's palsy, heart disease, such as atherosclerosis, heart failure, and hypertension, Parkinson's disease, type 1 and type 2 diabetes, attention deficit hyperactivity disorder (ADHD), autism, Alzheimer's disease, stroke, inflammatory pulmonary disease, inflammatory bowel disease, endometriosis, sunburn and an ever increasing number of other presentations.

A common link between these conditions appears to be the action of cytokine signalling molecules and, in particular, pro-inflammatory cytokines that are produced in within the cell due to the action of transcription factors such as NFκB. The pro-inflammatory cytokines tumour necrosis factor-alpha (TNF-α), interleukin-1 (IL-1) and interleukin-6 (IL-6) are key players in this inflammatory/immune response. Although the evidence for the role of the pro-inflammatory response in disease processes is strong and holds a great promise therapeutically, this has not translated into a significant number of therapeutic regimes to date. The small numbers of treatments that have been used to reduce the level of the pro-inflammatory response involve the production and use of monoclonal antibodies against TNF or IL-6. Results have been encouraging, but the treatment process itself is invasive, (requiring the antibody to be injected), occasionally results in significant adverse effects and involves high treatment costs. Therefore, the general use of antibody treatment for non-life-threatening diseases not a serious option.

Methylsulphonylmethane (MSM) is an organosulphur compound, also known as DMSO2, methyl sulphone, and dimethyl sulphone. Recent in vitro evidence suggests that MSM has an anti-inflammatory effect in murine macrophages by inhibiting the release of pro-inflammatory cytokines (Kim et al (2009) *Biol. Pharm. Bull* 32(4): 651-656). A further study suggests that MSM may have an analgesic and anti-inflammatory effect in osteoarthritis (Usha and Naidu (2004) *Clin. Drug Investig.* 24(6): 353-363). A preliminary study also indicates that oral treatment with MSM at relatively high dosages (2600 mg to 5200 mg per day) may reduce symptoms associated with seasonal allergic rhinitis (Barrager et (2002) *The Journal of Alternative and Complementary Medicine* 8(2): 167-173).

There is also some evidence that the monosaccharide glucosamine (alone or in combination with MSM) may improve the symptoms of osteoarthritis (Usha and Naidu (2004) *Clin. Drug Investig.* 24(6): 353-363). In vitro studies suggest that glucosamine inhibits the synthesis of proinflammatory mediators in chondrocytes (Largo et al (2003) *OsteoArthritis and Cartilage* 11:290-298).

A further compound, the amino acid glycine, has been shown in in vitro studies to have an immunomodulatory action, possibly by inhibiting TNF-α production (Wheeler et al (1999) *Cell. Mol. Life Sci.* 56: 843-856; Spittler et al (1999) *FASEB J* 13: 563-571).

US2007020218 describes the use of a combination of lysine, glucosamine, chondroitin and methylsulfonylmethane, taken orally to treat psoriasis.

There remains a need for effective, non-invasive therapies that can treat conditions related to the pro-inflammatory and dysfunctional immune response, particularly therapies that have few negative side-effects and are relatively low cost.

SUMMARY OF THE INVENTION

The present invention relates to the treatment of inflammatory or immune disorders using a combination of methylsulphonylmethane or a pharmaceutically acceptable salt or derivative thereof, glucosamine or a pharmaceutically acceptable salt or derivative thereof and glycine or a pharmaceutically acceptable salt or derivative thereof.

The inflammatory or immune disorder may include disorders mediated by an inflammatory response through the action of pro-inflammatory cytokines and their production through the action of intracellular transcription factors. Such disorders include, but are not limited to: inflammatory skin disorders, such as psoriasis, sunburn, reaction to insect bites and stings, eczema, pompholyx, pterygium, sebborheic dermatitis and solar keratosis; inflammation of the nasal and/or sinus passages or cavities; inflammatory eye disorders; and cardiac disease, such as hypertension.

In one aspect, the present invention provides a method of treating an inflammatory or immune disorder including administering to a subject in need of such treatment a pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof.

The methyl sulphonylmethane, glucosamine and glycine (or derivatives thereof) may be in any pharmaceutically acceptable form, including esters, amides, salts, solvates, pro-drugs, or metabolites provided they maintain therapeutic activity according to the present invention.

Suitably, the glucosamine (or pharmaceutically acceptable salt or derivative thereof) is in a form selected from the group consisting of glucosamine sulphate, glucosamine hydrochloride, glucosamine potassium sulphate and N-acetyl glucosamine.

Optionally, the glycine (or pharmaceutically acceptable salt or derivative thereof) is in a form selected from the group consisting of glycine ethyl ester, glycine sulphate and glycine hydrochloride.

In an embodiment of the invention, the inflammatory or immune disorder is selected from the group consisting of an inflammatory skin disorder, an inflammation of the nasal and/or sinus passages or cavities and a cardiac disease.

In a further embodiment, the inflammatory disorder or immune disorder is an inflammatory skin disorder.

In a yet further embodiment, the inflammatory or immune disorder is a disorder of the nasal and/or sinus passages or cavities.

In another aspect, the present invention provides a pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof, for use in treating an inflammatory or immune disorder.

In another aspect, the present invention provides a method of treating an inflammatory or immune disorder including administering to a subject in need of such treatment a pharmaceutical composition consisting of a therapeutically effective amount of methylsulphonylmethane or a pharmaceutically acceptable salt or derivative thereof, glucosamine or a pharmaceutically acceptable salt or derivative thereof and glycine or a pharmaceutically acceptable salt or derivative thereof, together with one or more pharmaceutically acceptable excipients and/or carriers.

In another aspect, the present invention provides a pharmaceutical composition consisting of methylsulphonylmethane or a pharmaceutically acceptable salt or derivative thereof, glucosamine or a pharmaceutically acceptable salt or derivative thereof and glycine or a pharmaceutically acceptable salt or derivative thereof, together with one or more pharmaceutically acceptable excipients and/or carriers, for use in treating an inflammatory or immune disorder.

DETAILED DESCRIPTION OF THE INVENTION

The terms "therapeutic agent", "agent" and "active agent" in this specification mean a substance that is intended for the treatment, prevention or modification of a state in a biological system. In the case of the method of the present invention, the therapeutic agent affects the symptoms of a disorder or condition related to an inflammatory response.

The term "pharmaceutical composition" as used in this specification includes all compositions including one or more therapeutic agents having an effect on the subject under treatment, including the alleviation or prevention of symptoms, together with one or more pharmaceutically acceptable excipients or carriers. The term "pharmaceutical composition" therefore encompasses compositions prepared to treat particular diseases or conditions and also nutrition supplements or nutraceuticals designed to improve various aspects of health.

The term "pharmaceutically acceptable" as used herein refers to compounds, compositions and dosage forms which are suitable for contact with human or animal tissues. A pharmaceutically acceptable excipient, or carrier, is a vehicle suitable for delivering a therapeutic agent to the site of action. The excipient or carrier must be compatible with the therapeutic agent and cause no or minimal negative effects on the subject being treated. Pharmaceutically acceptable excipients and carriers include lipid, solid fillers, diluents, solvents and encapsulating materials.

The terms "treating", "treat" and "treatment" refer to a therapeutic intervention that ameliorates a sign or symptom of an undesired physical or mental/emotional state, or a pathological condition, either before or after it has begun to develop. These terms also include: treatment designed for the relief of symptoms rather than the curing of a subject's undesired physical or mental/emotional state, or pathological condition; preventive treatment, that is, treatment directed to prevention of a subject's undesired physical or mental/emotional state, or pathological condition; and supportive treatment, that is, treatment employed to supplement another specific therapy directed toward the improvement of a subject's physical or mental/emotional state, or pathological condition.

As used herein, "preventing" (or "prevent" or "prevention") refers to a course of action initiated prior to the onset of a symptom, aspect, or characteristic of an undesired physical or mental/emotional state, or pathological condition, so as to prevent or reduce the symptom, aspect, or characteristic.

By "administration" is intended the introduction of a therapeutic agent (e.g., in a pharmaceutical composition) into a subject by a chosen route.

The term "therapeutically effective amount" describes a quantity of a specified therapeutic agent sufficient to achieve a desired effect in a subject being treated with that agent. The effective amount of an agent useful for treating or preventing an undesired physical or mental/emotional state or a pathological condition will be dependent on the subject being treated, the type and severity of the state or condition, and the manner of administration of the composition.

The term "subject" includes both human and veterinary subjects. For example, administration to a subject can include administration to a human subject or a veterinary subject. In an embodiment, the subject is a human. However, the compositions according to the present invention may be used as veterinary formulations for the treatment of domestic animals, such as cats and dogs, and agricultural animals, such as sheep, pigs, goats, cattle and horses etc.

The term "derivative" encompasses compounds derived from methylsulphonylmethane, glucosamine and glycine and having similarity with these compounds in terms of the required therapeutic activity according to the present invention. Derivatives include, but are not limited to, esters and amides, such as glycine ethyl ester and N-aceyl glucosamine.

The present inventor has determined that the combination of methylsulphonylmethane, glucosamine and glycine is surprisingly efficacious in the treatment of inflammatory disorders.

Without wishing to be bound by theory, it is believed that the combination of methylsulphonylmethane or a pharmaceutically acceptable salt or derivative thereof, glucosamine or a pharmaceutically acceptable salt or derivative thereof and glycine or a pharmaceutically acceptable salt or derivative thereof targets different aspects of the pathways regulating the production of proinflammatory cytokines. It is therefore believed the different mechanisms of action result in the synergistic effect of the combination of methylsulphonylmethane glucosamine and glycine. The combination of methylsulphonylmethane, glucosamine and glycine may therefore affect symptoms mediated by an inflammatory or other dysfunctional immune response at relatively low dosages.

In the case of solid compositions, it is understood that the therapeutic agents used in the methods of the invention may exist in different forms. For example, the compounds may exist in stable and metastable crystalline forms and amorphous forms, all of which are intended to be within the scope of the present invention.

The composition according to the invention may include any suitable pharmaceutically acceptable excipient or carrier. The pharmaceutically acceptable excipient or carrier can include any such pharmaceutical ingredient known in the art. Examples of suitable excipients or carriers are provided in the Handbook of Pharmaceutical Excipients (Rowe, Ray C; Sheskey, Paul J; Quinn, Marian eds, 6$^{th}$ Edition 2009, Pharmaceutical Press). Pharmaceutically acceptable excipients and carrier include, but are not limited to: talc; gum acacia; gelatine; magnesium trisilicate; keratin; colloidal silica; urea; buffers such as phosphate, citrate, acetate, and other organic acid salts; antioxidants such as ascorbic acid; peptides; proteins, such as, but not limited to, serum albumin, gelatin, or immunoglobulins; hydrophilic polymers such as, but not limited to, polyvinylpyrrolidinone; carbohydrates including cellulose or its derivatives, lactose, glucose and mannose; dextrins; potato or corn starch or starch paste; chelating agents such as, but not limited to, EDTA; sugar alcohols such as mannitol or sorbitol; and nonionic surfactants such as, but not limited to, the Tweens, Pluronics or polyethyleneglycol. In addition, the compositions may comprise auxiliary agents, such as, but not limited to, taste-enhancing agents, stabilizing agents, thickening agents, colouring agents and the like.

For some applications, such as where a transdermal or transmucosal delivery of the therapeutic agents is required, dimethyl sulphoxide (DMSO) may be used as an excipient in the pharmaceutical compositions used in the present invention. The inclusion of DMSO in certain formulations may assist in the delivery of the therapeutic agents across cell membranes into cells.

Accordingly, in an embodiment, the pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof further includes DMSO.

In another aspect, the present invention provides the use of methylsulphonylmethane or a pharmaceutically acceptable salt or derivative thereof, glucosamine or a pharmaceutically acceptable salt or derivative thereof and glycine or a pharmaceutically acceptable salt or derivative thereof in the manufacture of a medicament for the treatment of an inflammatory or immune disorder in a subject in need of such treatment.

In one embodiment, the medicament contains methylsulphonylmethane or a pharmaceutically acceptable salt or derivative thereof, glucosamine or a pharmaceutically acceptable salt or derivative thereof and glycine or a pharmaceutically acceptable salt or derivative thereof as the sole therapeutic agents.

In an embodiment, the medicament includes methylsuphonylmethane, glycine and glucosamine sulphate or N-actyl glucosamine.

In another embodiment, the medicament contains a further therapeutic agent in addition to the methylsulphonylmethane or a pharmaceutically acceptable salt or derivative thereof, glucosamine or a pharmaceutically acceptable salt or derivative thereof and glycine or a pharmaceutically acceptable salt or derivative thereof.

In one embodiment, the further therapeutic agent is nicotinamide, or a derivative thereof.

The inflammatory or immune disorder may be any disorder involving an inflammatory of dysfunctional immune response, particular a disorder involving a systemic inflammatory response mediated by pro-inflammatory cytokines, such as tumour necrosis factor alpha (TNF-α), interleukin-1 (IL-1) and interleukin-6 (Il-6). Such disorders may include, but are not limited to: allergies, including allergic reaction to insect bites and allergic rhinitis; skin disorders, including, but not limited to sunburn, psoriasis and dermatitis; stroke; Alzheimer's disease; and heart disease, such as hypertension.

In one embodiment, the inflammatory or immune disorder is selected from the group consisting of inflammatory skin disorders; inflammation of the nasal passages and cavity and sinusitis.

The present inventor has found that compositions including a combination of methylsulphonylmethane, glucosamine and glycine have a surprising efficacy in the treatment of certain skin disorders. In particular, topical treatment with the composition according to the present invention has been shown to be effective at treating or reducing the symptoms associated with inflammatory skin disorders such as psoriasis, scalp dermatitis, eczema (including pompholyx), seborrheic dermatitis, solar keratosis, cold sores and insect bites and stings. For some inflammatory skin conditions, oral treatment with a composition according to the present invention may also be used instead of or in addition to the topical treatment.

Further inflammatory skin disorders that may be treated with the composition in accordance with the present invention may include, but are not limited to, acne vulgaris, alopecia, folliculitis, poison ivy, acne inflammation and sunburn.

Accordingly, in a further embodiment, the inflammatory skin disorder is selected from the group consisting of: psoriasis; scalp dermatitis; eczema (including pompholyx); seborrheic dermatitis; solar keratosis; cold sores; response to insect bites and stings; acne vulgaris; alopecia; folliculitis; poison ivy; acne inflammation and sunburn.

The present inventor has also found that compositions including a combination of methylsulphonylmethane, glucosamine and glycine have a surprising efficacy in the treatment of conditions associated with inflammation of the nasal passages and sinuses. Such conditions may be associated with virus infection, allergies, or a response to low humidity conditions and use of continuous positive air pressure (CPAP) machines for the treatment of obstructive sleep apnoea. In particular, a nasal spray treatment with the composition according to the present invention has been shown to be effective at treating or reducing the symptoms associated with nasopharyngeal infection; nasal breathing difficulties with CPAP machines; allergic rhinitis; non allergic rhinitis and nasal congestion. Treatment with a composition according to the present invention may also reduce the duration and/or severity of symptoms associated with, or occurring as a result of infection with cold or influenza virus.

Accordingly, in a further embodiment, the inflammation of the nasal passages is caused by a condition selected from the group consisting of: allergic rhinitis; non-allergic rhinitis; exposure to low humidity environment; use of continuous positive air pressure machines; and infection.

The composition according to the present invention may also be useful in the topical treatment of inflammatory conditions of the eye, such as pterygium.

The present inventor has also found that compositions according to the present invention may also be useful in the treatment of cardiac disorders.

Accordingly, in a further embodiment, the inflammatory or immune disorder is a cardiac disorder. In a further embodiment, the cardiac disorder is hypertension.

In a further embodiment, the inflammatory or immune disorder is not an inflammatory condition affecting the joints.

In a further embodiment, the inflammatory or immune disorder is not arthritis.

A therapeutically effective amount of a pharmaceutical composition according to the invention may be administered in a single dose, or in several doses, for example daily, during a course of treatment. However, the frequency of administration is dependent on the preparation applied, the subject being treated, the severity and type of undesired physical or mental/emotional state, or pathological condition, and the manner of administration of the therapy or composition.

Various combinations of one or more additional therapeutic agents as known by one of skill in the art for the treatment and/or prevention of an inflammatory or immune disorder may be administered to a subject in need thereof in addition to a therapeutically effective amount of methylsulphonylmethane or a pharmaceutically acceptable salt or derivative thereof, glucosamine or a pharmaceutically acceptable salt or derivative thereof and glycine or a pharmaceutically acceptable salt or derivative thereof. In some embodiments, the combination including methylsulphonylmethane, glucosamine and glycine together with one or more additional therapeutic agents produces a synergistic effect in the treatment and/or prevention of an inflammatory disorder. Accordingly, the present invention also includes a method of enhancing the therapeutic efficacy of a therapeutic agent in treating an inflammatory or immune disorder.

The treatment of some inflammatory or immune disorders, such as inflammatory skin disorders, may be assisted by the inclusion of vitamin $B_{12}$ in the pharmaceutical composition according to the invention.

Accordingly, in a further aspect the present invention provides a method of treating an inflammatory skin disorder including administering to a subject in need of such treatment pharmaceutical composition including methylsulphonylmethane or a pharmaceutically acceptable salt or derivative thereof, glucosamine or a pharmaceutically acceptable salt or derivative thereof, glycine or a pharmaceutically acceptable salt or derivative thereof and vitamin $B_{12}$.

In an embodiment of this aspect of the invention, the inflammatory skin disorder is dermatitis.

In a further embodiment of this aspect of the invention, the inflammatory skin disorder is atopic dermatitis.

For certain applications, additional therapeutic agents may be used that assist in the treatment or alleviation of the symptoms of the particular inflammatory or immune disorder.

Accordingly, in a further aspect the present invention provides a method of treating an inflammatory skin disorder including administering to a subject in need of such treatment a therapeutically effective amount of methylsulphonylmethane or a pharmaceutically acceptable salt or derivative thereof, glucosamine or a pharmaceutically acceptable salt or derivative thereof and glycine or a pharmaceutically acceptable salt or derivative thereof together with a further therapeutic agent.

In one embodiment, the further therapeutic agent is nicotinamide, or a derivative thereof. In a preferred embodiment, methylsulphonylmethane or a pharmaceutically acceptable salt or derivative thereof, glucosamine or a pharmaceutically acceptable salt or derivative thereof and glycine or a pharmaceutically acceptable salt or derivative thereof is administered in a topical formulation and the nicotinamide is administered orally. In a further preferred embodiment, the nicotinamide is included in a topical formulation together with methylsulphonylmethane or a pharmaceutically acceptable salt or derivative thereof, glucosamine or a pharmaceutically acceptable salt or derivative thereof and glycine or a pharmaceutically acceptable salt or derivative thereof.

In one embodiment, the further therapeutic agent is not vitamin $B_{12}$.

The therapeutic agents of the present disclosure can be administered by any conventional method available for pharmaceutical compositions.

The pharmaceutical composition can be, for example, in an aerosol, solid, semi-solid, or liquid form which contains methylsulphonylmethane or a pharmaceutically acceptable salt or derivative thereof, glucosamine or a pharmaceutically acceptable salt or derivative thereof and glycine or a pharmaceutically acceptable salt or derivative thereof. In addition, the compositions may be used in an admixture with an appropriate pharmaceutically acceptable excipient or carrier. Such pharmaceutically acceptable carriers include, but are not limited to, organic or inorganic carriers, excipients or diluents suitable for pharmaceutical applications. The active ingredients may be compounded, for example, with the usual non-toxic pharmaceutically acceptable carriers, excipients or diluents for tablets, pellets, capsules, inhalants, suppositories, solutions, emulsions, suspensions, aerosols, and any other form suitable for use.

The compositions may be prepared for storage or administration by mixing the active ingredients, each having a desired degree of purity, with physiologically acceptable carriers, excipients, stabilizers, auxiliary agents, and the like, as is known in the art. Such compositions may be provided in sustained release or timed release formulations.

The compositions according to the present invention may be administered orally in solid dosage forms, such as capsules, tablets, and powders, or in liquid dosage forms, such as elixirs, syrups and suspensions. Furthermore the compositions containing the therapeutic agents may be administered parenterally, in sterile liquid dosage forms, by transmucosal delivery via solid, liquid or aerosol forms or transdermally via a patch mechanism or ointment. Various types of transmucosal administration include respiratory tract mucosal administration, nasal mucosal administration, oral transmucosal (such as sublingual and buccal) administration, and rectal transmucosal administration.

For preparing solid compositions such as, but not limited to, tablets or capsules, methylsulphonylmethane or a pharmaceutically acceptable salt or derivative thereof, glucosamine or a pharmaceutically acceptable salt or derivative thereof and glycine or a pharmaceutically acceptable salt or derivative thereof may be mixed with appropriate pharmaceutically acceptable carriers, such as conventional tableting ingredients (e.g., lactose, sucrose, mannitol, corn starch, potato starch, alginic acid, microcrystalline cellulose, acacia, gelatin, gums, colloidal silicon dioxide, croscarmellose sodium, talc, sorbitol, stearic acid magnesium stearate, calcium stearate, zinc stearate, stearic acid, and dicalcium phosphate), other excipients, colorants, diluents, buffering agents, disintegrating agents, moistening agents, preservatives, flavouring agents, and pharmacologically compatible carriers, as well as diluents (e.g., water, saline or buffering solutions) to form a substantially homogenous composition. The substantially homogenous composition means the components are dispersed evenly throughout the composition so that the composition may be readily subdivided into equally effective unit dosage forms such as tablets, pills and capsules.

The solid compositions described may be coated or otherwise compounded to provide a dosage form affording the advantage of prolonged action. For example, tablets or pills can comprise an inner dosage and an outer dosage component, the latter being in the form of an envelope over the former. The two components can be separated by an enteric layer which serves to resist disintegration in the stomach and permits the inner component to pass intact through the stomach or to be delayed in release. A variety of materials can be used for such enteric layers or coatings such materials including a number of polymeric acids and mixtures of polymeric acids with such materials as shellac, cetyl alcohol and cellulose acetate.

The active ingredients may also be formulated in rectal compositions such as suppositories or retention enemas, for example, containing conventional suppository bases such as cocoa butter or other glycerides. The solid compositions may also comprise a capsule, such as hard- or soft-shelled gelatin type containing, for example, surfactants, lubricants, and inert fillers, such as lactose, sucrose, calcium phosphate, and corn starch.

For intranasal administration, intrapulmonary administration or administration by other modes of inhalation, the pharmaceutical compositions may be delivered in the form of a solution or suspension from a pump spray container or as an aerosol spray presentation from a pressurized container or nebulizer, with the use of a suitable propellant (e.g., dichlorodifluoromethane, trichlorofluoromethane, dichlorotetrafluoroethane, nitrogen, propane, carbon dioxide, or other suitable gas) or as a dry powder. In the case of an aerosol or dry powder format, the amount (dose) of the composition delivered may be determined by providing a valve to deliver a metered amount.

Liquid forms may be administered orally, parenterally or via transmucosal administration. Suitable forms for liquid administration include aqueous solutions, suitably flavoured syrups, aqueous or oil suspensions, and flavoured emulsions with edible oils such as cottonseed oil, sesame oil, coconut oil, or peanut oil, as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone, and gelatin. Such liquid preparations may be prepared by conventional means with pharmaceutically acceptable additives such as suspending agents (e.g., sorbitol syrup, methyl cellulose or hydrogenated edible fats), emulsifying agents (e.g., lecithin or acacia), non-aqueous vehicles (e.g., almond oil, oily esters or ethyl alcohol), preservatives (e.g., methyl or propyl p-hydroxybenzoates or sorbic acid), and artificial or natural colours and/or sweeteners.

Liquid formulations may include diluents, such as water and alcohols (e.g., ethanol, benzyl alcohol, propylene glycol, glycerin, and the polyethylene alcohols), either with or without the addition of a pharmaceutically acceptable surfactant, suspending agent, or emulsifying agent.

For buccal or sublingual administration, the composition according to the present invention may take the form of tablets or lozenges formulated in conventional manners. Lozenge forms can comprise the active ingredient in a flavour, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The pharmaceutical compositions may be formulated for parenteral administration. Parenteral administration includes, but is not limited to, intravenous administration, subcutaneous administration, intramuscular administration, intradermal administration, intrathecal administration, intraarticular administration, intracardiac administration, retrobulbar administration, and administration via implants, such as sustained release implants.

The compositions according to the present invention may be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known in the art.

Therapeutic treatments can include a therapeutically effective amount of methylsulphonylmethane or a pharmaceutically acceptable salt or derivative thereof, glucosamine or a pharmaceutically acceptable salt or derivative thereof and glycine or a pharmaceutically acceptable salt or derivative thereof necessary to prevent or treat an undesired physical or mental/emotional state, or a pathological condition, or for improving cognitive performance. Ideally, a therapeutically effective amount of an agent is an amount sufficient to produce the desired result without causing a substantial cytotoxic effect in the subject. The effective amount of an agent useful for preventing or treating an undesired physical or mental/emotional state, or a pathological condition, or for improving cognitive performance, will be dependent on the subject being treated, the severity of the state or condition, and the manner of administration of the therapeutic composition. Effective amounts can be determined by standard clinical techniques.

For example, when administering a composition comprising according to the invention, the precise dose to be employed in the formulation will depend on the route of administration, and should be decided according to the judgment of the health care practitioner and each subject's circumstances. The concentration of an active ingredient in a topical composition (such as an ointment, cream, gel, lotion, shampoo or lip balm) is typically from about 0.1% to about 10% (by weight relative to the total weight of the topical composition); for example, from about 0.5% to about 8%, from about 1% to about 6%, and from about 2% to about 5%. Within the ranges, higher concentrations allow a suitable dosage to be achieved while applying the lotion, ointment, gel, or cream in a lesser amount or with less frequency.

In other embodiments, a dosage range for non-topical administration (such as oral administration, or intravenous or intraperitoneal injection) of a composition according to the invention is from about 0.1 to about 200 mg/kg body weight for each active agent in single or divided doses; for example from about 1 to about 100 mg/kg, from about 2 to about 50 mg/kg, from about 3 to about 25 mg/kg, or from about 5 to about 10 mg/kg.

Acceptable daily dosages of the active ingredients of the compositions of the present invention include between 100 and 6,000 mg of methylsulphonylmethane (e.g., 150 mg, 200 mg, 250 mg, 500 mg, 600 mg 800 mg, 1,000 mg, 1,500 mg, 2,000 mg, 2,500 mg, 3,000 mg, 3,500 mg, 4,000 mg, 4,500 mg, 5,000 mg, and 5,500 mg), between 100 and 6,000 mg of glucosamine (e.g., 150 mg, 200 mg, 250 mg, 500 mg, 600 mg 800 mg, 1,000 mg, 1,500 mg, 2,000 mg, 2,500 mg, 3,000 mg, 3,500 mg, 4,000 mg, 4,500 mg, 5,000 mg, and 5,500 mg), and between 100 and 6,000 mg of glycine (150 mg, 200 mg, 250 mg, 500 mg, 600 mg 800 mg, 1,000 mg, 1,500 mg, 2,000 mg, 2,500 mg, 3,000 mg, 3,500 mg, 4,000 mg, 4,500 mg, 5,000 mg, and 5,500 mg).

The compositions of the present disclosure can be administered at about the same dose throughout a treatment period, in an escalating dose regimen, or in a loading-dose regime (for example, in which the loading dose is about two to five times the maintenance dose). In some embodiments, the dose is varied during the course of a treatment based on the condition of the subject being treated, the apparent response to the therapy, and/or other factors as judged by one of ordinary skill in the art. In some embodiments long-term treatment with a disclosed pharmaceutical composition is contemplated.

In one embodiment, the composition includes between 100 and 6,000 mg of methylsulphonylmethane (e.g., 150 mg, 200 mg, 250 mg, 500 mg, 600 mg 800 mg, 1,000 mg, 1,500 mg, 2,000 mg, 2,500 mg, 3,000 mg, 3,500 mg, 4,000 mg, 4,500 mg, 5,000 mg, and 5,500 mg), between 100 and 6,000 mg of glucosamine (e.g., 150 mg, 200 mg, 250 mg, 500 mg, 600 mg 800 mg, 1,000 mg, 1,500 mg, 2,000 mg, 2,500 mg, 3,000 mg, 3,500 mg, 4,000 mg, 4,500 mg, 5,000 mg, and 5,500 mg), and between 100 and 6,000 mg of glycine (150 mg, 200 mg, 250 mg, 500 mg, 600 mg 800 mg, 1,000 mg, 1,500 mg, 2,000 mg, 2,500 mg, 3,000 mg, 3,500 mg, 4,000 mg, 4,500 mg, 5,000 mg, and 5,500 mg).

In an embodiment, the composition includes between 100 and 1000 mg of methylsulphonylmethane (MSM), between 100 and 1000 mg of glycosamine and between 100 and 1000 mg of glycine.

Different ratios of the active ingredients may be used in pharmaceutical compositions in accordance with the present invention, depending on the condition to be treated and the mode of administration. In one embodiment, the ratio of glucosamine:MSM:glycine is in the range of 0.5-4:0.5-4:0.5-4 on a weight basis. In a further embodiment, the ratio of glucosamine:MSM:glycine is in the range of 1-3:1-3:1-3 on a weight basis. In a preferred embodiment, the glucosamine is present in a greater proportion than the each of the amounts of MSM and glycine. In a further preferred embodiment, the MSM is present in a greater proportion than the each of the amounts of glucosamine and glycine.

In an embodiment, the ratio of glucosamine:MSM:glycine is 2.0:1.5:1.5 on a weight basis.

In a further embodiment, the ratio of glucosamine:MSM:glycine is 1.5:2.0:1.5.

In a yet further embodiment, the composition in accordance with the present invention includes between 400 and 500 mg of glucosamine, between 200 and 300 mg of MSM and between 200 and 300 mg of glycine.

In a further embodiment, the composition in accordance with the present invention includes between 200 and 300 mg of glucosamine, between 400 and 500 mg of MSM and between 200 and 300 mg of glycine.

In a further embodiment, the pharmaceutical composition is in the form of a solid oral dosage form including: 450 mg glucosamine, 225 mg MSM and 225 mg glycine.

In a further embodiment, the pharmaceutical composition is in the form of a solid oral dosage form including: 225 mg glucosamine, 450 mg MSM and 225 mg glycine.

In a further embodiment, the pharmaceutical composition is in the form of a topical dosage form including 20 mg glucosamine; 15 mg MSM and 15 mg glycine per gram of lotion, cream or solution.

In a further embodiment, the pharmaceutical composition is in the form of a nasal spray dosage form including 0.8 mg glucosamine; 0.6 mg MSM and 0.6 mg glycine per ml of liquid spray formulation The following tables provide preferred dosages of compositions according to the invention.

TABLE 1

Oral formulations: suitable dosages

| Agent | Suitable dosage range |
|---|---|
| MSM | 100 to 500 mg per day |
| glucosamine | 100 to 500 mg per day |
| Glycine | 100 to 500 mg per day |

TABLE 2

Nasal spray formulations: suitable dosages

| Agent | Suitable dosage range |
|---|---|
| MSM | 0.001 to 0.008 mg per spray |
| glucosamine | 0.002 to 0.012 mg per spray |
| Glycine | 0.001 to 0.008 mg per spray |

TABLE 3

Topical formulations: suitable dosages

| Agent | Suitable dosage range |
|---|---|
| MSM | 5-30 mg per g cream/lotion |
| glucosamine | 5-30 mg per g cream/lotion |
| Glycine | 5-30 mg per g cream/lotion |

For certain applications, nicotinamide may be included as a further active ingredient in a topical formulation.

The nicotinamde may be included in a ratio of nicotinamide:glucosamine:MSM:glycine of 2.0:1.0:1.5:1.5 on a weight basis. A topical formulation including nicotinamide may include 5-30 mg nicotinamide per gram of cream or lotion.

For treating skin conditions caused by an inflammatory or dysfunctional immune response, the pharmaceutical composition according to the present invention may be in the form of a cream, lotion (including a spray lotion), solution (including a solution suitable for application by spraying), shampoo or lip balm.

Accordingly, in another aspect, the present invention provides a pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof, for treating an inflammatory or immune disorder of the skin, wherein the composition is suitable for topical administration.

In an embodiment, the composition is in a formulation selected from the group consisting of: a lotion; a solution; a cream; a shampoo; and a lip balm The use of a pharmaceutical composition in accordance with the present invention may result in an improvement of skin health in the area otherwise affected by the inflammatory or immune disorder.

Accordingly, in a further aspect the present invention provides a method of improving skin health in a subject currently or previously afflicted by an inflammatory skin disorder, including administering to the subject a therapeutically effective amount of a pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof, wherein the composition is suitable for topical administration.

In one embodiment, the inflammatory skin disorder is selected from the group consisting of seborrheic dermatitis, seborrheic keratosis, psoriasis, atopic dermatitis, cold sores (herpes simplex), shingles (herpes zoster), acne vulgaris, inflammatory response to bites and stings, sunburn, and solar keratosis.

In a further embodiment, the inflammatory skin disorder is psoriasis.

In a further embodiment, the cream, lotion or spray includes methylsulphonylmethane or a pharmaceutically acceptable salt or derivative thereof, glucosamine or a pharmaceutically acceptable salt or derivative thereof and glycine or a pharmaceutically acceptable salt or derivative thereof, as the sole therapeutic agents.

In a further embodiment, composition suitable for topical administration includes methylsulphonylmethane or a pharmaceutically acceptable salt or derivative thereof, glucosamine or a pharmaceutically acceptable salt or derivative thereof and glycine or a pharmaceutically acceptable salt or derivative thereof and nicotinamide, or a derivative thereof.

In another aspect, the present invention provides a method of treating an inflammatory skin disorder including administering to a subject in need of such treatment a therapeutically effective amount of a pharmaceutical cream, lotion or spray consisting of methylsulphonylmethane or a pharmaceutically acceptable salt or derivative thereof, glucosamine or a pharmaceutically acceptable salt or derivative thereof and glycine or a pharmaceutically acceptable salt or derivative thereof, together with one or more pharmaceutically acceptable excipients and/or diluents.

For certain disorders, the pharmaceutical composition according to the present invention may be administered to the patient orally as a sole treatment or as an adjuvant to topical treatment. In one embodiment, the present invention provides methylsulphonylmethane or a pharmaceutically acceptable salt or derivative thereof, glucosamine or a pharmaceutically acceptable salt or derivative thereof and glycine or a pharmaceutically acceptable salt or derivative thereof in both topical and oral formulations for the combined treatment of an inflammatory or immune disorder. In one embodiment, the inflammatory or immune disorder is a skin disorder, such as psoriasis. In a further embodiment, the inflammatory or immune disorder is psoriatic arthritis.

For treating inflammatory or dysfunctional immune response conditions of the nasal passages or sinuses, such as allergic or non-allergic rhinitis and sinusitis, the pharmaceutical composition according to the present invention may be in the form of a nasal spray. The spray may be administered by a spray pump or pressurised aerosol. The inflammatory or immune disorder of the nasal passages or sinuses could be caused by infection, allergy or exposure to low humidity environments.

Accordingly, in another aspect the present invention provides a pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof, for use in treating an inflammatory or immune disorder of the nasal passages or sinuses, wherein the composition is a form suitable for administration by spray or aerosol.

The treatment with the composition according to the present invention may open the nasal passages thereby allowing improved passage of air through the nasal passages.

In a further embodiment, the inflammatory or immune disorder of the nasal passages is related to, or a consequence of, a cold or influenza virus infection. Treatment with a composition according to the present invention may reduce the severity or duration of symptoms associated with colds or influenza.

In a further embodiment, the inflammatory or immune disorder of the nasal passages or sinuses is caused by an allergic reaction.

In a further embodiment, the inflammatory or immune disorder of the nasal passages or sinuses caused by an allergic reaction is allergic rhinitis.

In one embodiment, the nasal spray includes methylsulphonylmethane, glycine and glucosamine sulphate or N-acetyl glucosamine.

In a further embodiment, the nasal spray includes methylsulphonylmethane or a pharmaceutically acceptable salt or derivative thereof, glucosamine or a pharmaceutically acceptable salt or derivative thereof and glycine or a pharmaceutically acceptable salt or derivative thereof together with a further therapeutic agent. In one embodiment, the further therapeutic agent is a decongestant. Examples of suitable decongestants include, but are not limited to: oxymetazoline; naphazoline; phenylephrine; phenylpropanolamine; propylhexedrine; synephrine; tetrahydrozoline and xylometazoline.

For treating cardiac conditions resulting from an inflammatory response or dysfunctional immune system, such as hypertension, the pharmaceutical composition according to the present invention may be provided orally or parenterally.

In an embodiment, for treating cardiac conditions resulting from an inflammatory response or dysfunctional immune system, such as hypertension, the pharmaceutical composition according to the present invention is provided orally in the form of a tablet or capsule.

The treatment according to the present invention may improve general cardiac health by, for example, lowering blood pressure.

Accordingly, in a further aspect, the present invention provides a method of improving cardiac health in a subject currently or previously afflicted by a cardiac disorder resulting from an inflammatory or dysfunctional immune response, including administering to the subject a therapeutically effective amount of a pharmaceutical composition including methylsulphonylmethane or a pharmaceutically acceptable salt or derivative thereof, glucosamine or a pharmaceutically acceptable salt or derivative thereof and glycine or a pharmaceutically acceptable salt or derivative thereof.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any compound referred to herein is also intended to represent unlabelled forms as well as isotopically labelled forms of the compounds isotopically labelled compounds have the known structures except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labelled compounds, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labelled compound may be particularly desirable for PET or SPECT studies. Isotopically labelled compounds of this invention and prodrugs thereof can generally be prepared by known techniques by substituting a readily available isotopically labelled reagent for a non-isotopically labelled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labelled compounds can generally be prepared by conventional techniques known to those skilled in the art.

Compounds of the present invention are either obtained in the free form, as a salt thereof, or as prodrug derivatives thereof. Furthermore, the compounds may be in a hydrated form or a solvated form. In such forms, the compound may have associated with it one or more molecules of water and/or one or more molecules of a solvent. Where the compound or salt thereof is in a crystal form, the water and/or solvent molecule(s) may be incorporated into the crystal lattice.

So that the present invention may be more readily understood and put into practical effect, the skilled person is referred to the following non-limiting examples.

EXAMPLES

Example 1

Topical Formulations

The following topical formulations were prepared:

| Ingredients | 0% w/v | 2% w/v | 5% w/v |
| --- | --- | --- | --- |
| MSM | 0 g | 0.6 g | 1.5 g |
| Glucosamine | 0 g | 0.8 g | 2.0 g |
| Glycine | 0 g | 0.6 g | 1.5 g |
| Base cream* | 100 ml | 98 ml | 96 ml |
| Total | 100 ml | 100 ml | 100 ml |

*The base cream was a commercially available water based emulsion cream.

Patients with clinically diagnosed psoriasis were provided with one of the three concentrations (0%, 2% or 5%) of the topical formulations listed above, using a randomized system to determine which patient received which concentration. The patients were given instructions to apply the cream at liberty to three similar areas on the skin, i.e. arm/arm or leg/leg, and not changes by observing any improvement in the lesions over 1 week. After 1 week of application, the patients using the 0% cream showed no improvement in their symptoms and the patients using the 2% cream showed some improvement. The patients using the 5% cream experienced good improvement in their condition, with 67% of this group showing a significant resolution of their symptoms.

Further trials were performed on patients with other inflammatory skin conditions. Conditions such as the inflammation associated with insect bites, leech bites and seborrheic dermatitis, seborrheic keratosis, atopic dermatitis and acne responded well to both the 2% and 5% treatments.

Example 2

Nasal Spray Formulations

A nasal spray formulation was prepared using a 0.2% formulation of MSM, glucosamine and glycine (with a ratio of 2:1.5:1.5 glucosamine sulphate:glycine:methylsulphonylmethane) in a 0.9% saline solution with benzalkonium chloride as a preservative. This spray was given to patients diagnosed with allergic and non-allergic rhinitis. 10 minutes after treatment with the nasal spray using two sprays per nostril, a majority (approximately 90%) of the patients reported clear and open nasal airways.

Example 3

Oral Formulations

Solid oral formulations of pharmaceutical compositions accordingly to the present invention may be prepared with the following proportions per tablet:

| Ingredients | |
|---|---|
| MSM | 225 mg |
| Glucosamine | 450 mg |
| Glycine | 225 mg |

For some applications, such as for the treatment and/or prevention of hypertension, solid oral formulations of pharmaceutical compositions accordingly to the present invention may be prepared with the following proportions per tablet:

| Ingredients | |
|---|---|
| MSM | 450 mg |
| Glucosamine | 225 mg |
| Glycine | 225 mg |

Six patients with diagnosed hypertension were receiving treatment with a combination of MSM, glucosamine and glycine. After treatment, each of these patients demonstrated a significant lowering of blood pressure. The reduction in blood pressure was sufficient to enable a reduction of the patient's additional anti-hypertensive medication.

Example 4

Nasal Spray 0.2%

Allergic and Non-Allergic Rhinitis

A nasal spray was prepared using a 0.2% formulation of the MSM, glucosamine sulphate and glycine mixture (with a ratio of 2:1.5:1.5 glucosamine sulphate:glycine:methylsulphonylmethane) in a 0.9% saline solution with benzalkonium chloride as a preservative.

The effect of this 0.2% nasal spray formulation on allergic and non-allergic rhinitis conditions was tested.

The spray was well tolerated with no adverse reactions being reported in a negative control group. This group consisted of 10 adults with no history of allergic or non-allergic rhinitis. The group used the spray twice a day for 28 days by instilling two sprays to each nostril twice per day. Participants kept a symptom diary and there were no reports of any adverse effects during the trial period. This was a significant finding when compared with the side effects of nasal decongestants that would be expected for such a trial.

The treatment group consisted of 9 adults with rhinitis conditions. In the treatment group good symptomatic clearance was achieved in a short time after instillation of the spray into the effected nostrils. Individuals that were chronically complaining of inability to breathe effectively, due to chronic inflammation associated with septal damage or with seasonal rhinitis, reported having a significant reduction of symptoms and/or improved air flow. Some of the participants had years of reduced nasal airflow associated with little relief, even from surgery or steroids.

Combination Treatment with Decongestant

The MSM, glucosamine sulphate and glycine 0.2% nasal spray may be used in a combination treatment with a decongestant. Use of a decongestant in combination with the MSM, glucosamine sulphate and glycine nasal spray may facilitate the contact between the MSM, glucosamine sulphate and glycine nasal spray and mucous membranes by reducing mucous production and therefore the mucous covering of the membranes.

A trial of 4 patients using a 50/50 solution of the 0.2% MSM, glucosamine sulphate and glycine nasal spray and 0.5% oxymetazoline decongestant was able to reduce the both the mucous production and the inflammation that gave rise to the mucous production in the first place. The resultant clinical improvement was superior to the effect that would be achieved with either the decongestant, or the MSM, glucosamine sulphate and glycine nasal spray alone.

CPAP Users and Improvement of Symptoms in Low Humidity Conditions

Individuals who experience dry environments through air travel, use continuous positive airway pressure (CPAP) machines, or experience other environmental conditions that can irritate the nasal and sinus passages can have associated inflammation. Dry air can cause the sinuses to become inflamed, cutting off the ability to breathe normally. The use of saline sprays to increase the humidity have had limited success as the spray does not reduce the inflammatory process and there is only a transient improvement.

Trials with individuals on CPAP machines and others flying for long distances has shown benefit of using the 0.2% MSM, glucosamine sulphate and glycine nasal spray. The best results were found using the spray at the start of the night with CPAP or before taking off with flying. The benefit was long lived in both cases.

Example 5

5% Spray for the Treatment of Psoriasis and Solar Keratosis

The use of a 5% MSM, glucosamine sulphate and glycine mixture (with a ratio of 2:1.5:1.5 glucosamine sulphate:glycine:methylsulphonylmethane) in a 0.9% saline solution carrier has been found to be very useful in treating conditions that are difficult to treat using creams or lotions. For example, creams or lotions can have difficulty in penetrating the hair for treatment of the scalp region. Trials using the spray formulation in the management of scalp psoriasis and solar keratosis have been encouraging.

Trials with the 5% MSM, glucosamine sulphate and glycine spray were well tolerated and resulted in good efficacy in managing symptoms, such as pruritus, erythema, soreness and scaling. The spray was able to penetrate the hair to the affected areas more effectively than cream alone. The spray provided a good coverage, was simple to massage in, and was found to be just as efficacious as the 5% MSM, glucosamine and glycine topical cream.

Example 6

5% Spray Treatment of Insect Bites and Stings

Allergy to insect bites and stings is a significant problem with many people experiencing significant discomfort associated with the injection of venom or other irritating substances under the skin. Typically there will be swelling, pruritus, pain and itching all associated with the inflammatory process put up as a defence to these substances.

Treatment with 5% MSM, glucosamine sulphate and glycine spray reduced the reaction significantly over a short period of time in green ant bites, mosquito and sand fly bites also tick and leech bites. The response to the treatment was discernible within 10 minutes of application. One participant treated for a large number of mosquito bites had no discernible signs of bites an hour after treatment, but still had a large inflammatory reaction in a number of bites that had not been treated.

Example 7

5% Spray Reduces the Symptoms of Nasopharyngeal Infection

5% MSM, glucosamine sulphate and glycine spray has with a number of participants reduced the symptoms in 5 patients with nasopharyngeal infection. The spray was administered by spraying and inhaling through the mouth. Reduction of symptoms and duration of infection was seen in these individuals compared to a cohort of individuals who were experiencing early symptoms of infection at the same time as those treated, but who did not take MSM, glucosamine and glycine treatment. It would appear therefore that MSM, glucosamine sulphate and glycine spray may reduce the duration and severity of acute nasopharyngeal infections.

Example 8

Treatments with 5% Topical Cream

A cream consisting of 5% glucosamine sulphate, glycine and MSM (in a ratio of 2:1.5:1.5) in an inert carrier has been trialed in the treatment of a variety of inflammatory skin disorders (ISD). This trial consisted of 29 participants having the following disorders:
  Eczema (6)
  Sebborheic dermatitis (3)
  Psoriasis (7)
  Solar keratosis (5)
  Other non specific rash (8)
  Eczema is a common inflammatory skin disorder with anything up to 20% prevalence in countries such as UK. As with most ISDs, treatment can be difficult and can have significant side effects. Because of the toxicity of a number of these treatments short term use is usually recommended. This results in poor resolution of the condition and recurrence on regular intervals.

Trials using the glucosamine sulphate, glycine and MSM cream show minimal side effects when compared with existing treatments and as a result can be used for extended periods of time and even as a way of reducing the number of times there is recurrence.

A patient with a difficult and persistent case of pompholyx (dyshidrotic eczema or vesicular hand eczema) and had tried many creams and lotions before. This participant had good resolution of his condition within 24 hours of applying the first treatment of glucosamine sulphate, glycine and MSM cream 5% cream.

All participants trialed the glucosamine sulphate, glycine and MSM 5% cream to treat eczema had tried many creams and emollients in the past with little success. Every one of the participants concluded that they had not experienced a treatment with such speedy and positive results. Participants reported resolution of symptoms with the glucosamine sulphate, glycine and MSM 5% cream often in the first 1 to 2 days. Often they report that they have tried everything without the same results.

Psoriasis is a significant ISD with many social as well as medical complications. People report a variety of disfiguring skin lesions that can prevent them from normal social interaction. Even with expensive treatments, lesions typically will not resolve to a level that is that indicates to the user that there has been good resolution. Even though the lesions appear to have been resolved the skin still feels bumpy and rough to the patient.

This level of efficacy was also noted in mixed ISD such as seborrheic dermatitis psoriasis. Also there was a similar efficacy in trials using 5% glucosamine sulphate, glycine and MSM cream on insect bites to that of using the 5% glucosamine sulphate, glycine and MSM spray.

Example 9

Treatment of Psoriatic Arthritis Using a Combination Topical/Oral Treatment

In two cases psoriasis associated with psoriatic arthritis was able to be controlled with the glucosamine sulphate, glycine and MSM 5% cream enabling resolution of the psoriatic lesions a few weeks after commencing treatment. Furthermore, a combination oral and topical treatment with MSM, glucosamine sulphate and glycine was found to reduce not only the psoriasis lesions, but also to improve the mobility of joints in patients with psoriatic arthritis.

Example 10

Treatment of the Eye Disease Pterygium

A patient presented with a long standing case of bilateral pterygium. This was painful and required the wearing of dark glasses due to photophobia. There were no options for the patient other than surgery. The surgical procedure has a good outcome but a recurrence in a large proportion of those receiving this treatment is common and recurrent pterygium grow more aggressively across the eye.

The patient was provided with an eye drop composition including nicotinamide, MSM, glycine and glucosamine sulphate in a ratio of 2.0:1.5:1.5:1.0 as a 0.025% w/v in eye irrigation fluid (artificial tears).

After two weeks of one daily treatment, it was noted that the redness had almost all disappeared and the pterygium itself had diminished by approximately 50%.

It is to be understood that various alterations, modifications and/or additions may be made without departing from the spirit of the present invention described.

Documents cited in this specification are for reference purposes only and their inclusion is not an acknowledgment that they form part of the common general knowledge in the relevant art.

TABLE 1

Summary of treatments using various formulations of glucosamine sulphate, glycine and MSM

| | Cream 5% (CR) | Capsules (CP) | CR and CP | Nicotin- amide oral (NC) | CR and NC | Shampoo 5% | Spray 5% (SP5) | Spray 0.5% (SP0.5) | SP 0.5 with de- congestant |
|---|---|---|---|---|---|---|---|---|---|
| Psoriasis | ++ | ++ | ++++ | + | ++++ | +++ | +++ | NT | NT |
| Scalp dermatitis | +++ | ++ | ++++ | NT | NT | ++++ | ++++ | NT | NT |
| Psoriatic arthritis | +++ | ++ | +++++ | | | | +++ | NT | NT |
| Eczema including Pompholyx | +++ | NT | NT | NT | NT | NT | +++ | NT | NT |
| Seborrheic dermatitis | ++ | +++ | ++++ | NT | NT | +++ | NT | NT | NT |
| Solar Keratosis | ++++ | NT | NT | + | ++++ | NT | +++ | NT | NT |
| Herpes simplex Cold sores | ++++ | NT | NT | NT | NT | NT | | | |
| Insect bites and stings | +++ | NT | NT | NT | NT | NT | ++++ | +++ | NT |
| Nasopharyngeal infection | NT | NT | NT | NT | NT | NT | ++++ | NT | NT |
| Nasal breathing difficulties with CPAP machines | NT | NT | NT | NT | NT | NT | NT | +++ | NT |
| Allergic rhinitis | NT | ++ | NT | NT | NT | NT | NT | ++++ | NT |
| Non allergic rhinitis | NT | NT | NT | NT | NT | NT | NT | ++ | ++++ |
| Nasal congestion | NT | NT | NT | NT | NT | NT | NT | ++ | ++++ |

The + values in the table represent a qualitative assessment of the treatment of symptoms in the patient groups tests with 5+ indicating the greatest improvement in symptoms; NT: not tested.

The invention claimed is:

1. A method of treating an inflammatory or immune disorder including administering to a subject in need of such treatment a pharmaceutical composition comprising an active agent which consists essentially of a combination of:
   (a) methylsulphonylmethane or a pharmaceutically acceptable salt thereof;
   (b) glucosamine, a glucosamine derivative or a pharmaceutically acceptable salt thereof, wherein the glucosamine derivative is selected from glucosamine sulfate, N-acetyl glucosamine, glucosamine hydrochloride, glucosamine potassium sulphate, and mixtures thereof; and
   (c) glycine, a glycine derivative or a pharmaceutically acceptable salt thereof, wherein the glycine derivative is selected from glycine ethyl ester, glycine sulphate, glycine hydrochloride and mixtures thereof,
   wherein the inflammatory or immune disorder is selected from inflammatory skin disorders; inflammation of the nasal and/or sinus passages or cavities; inflammatory eye disorders; and cardiac disorders.

2. The method according to claim 1, wherein the inflammatory or immune disorder is an inflammatory skin disorder.

3. The method according to claim 1, wherein the inflammatory or immune disorder is an inflammation of the nasal and/or sinus passages or cavities.

4. The method according to claim 1, wherein the inflammatory or immune disorder is an inflammatory eye disorder.

5. The method according to claim 1, wherein the inflammatory or immune disorder is a cardiac disorder.

6. The method according to claim 1, wherein the pharmaceutical composition is formulated for topical administration and the method includes topical administration of the composition.

7. The method according to claim 1, wherein the pharmaceutical composition is formulated for administration as a nasal spray and the method includes nasal administration of the composition.

8. The method according to claim 1, wherein the active agent includes between 100 mg and 1000 mg of methylsulphonylmethane or a pharmaceutically acceptable salt thereof, between 100 mg and 1000 mg of glucosamine, said glucosamine derivative or a pharmaceutically acceptable salt or derivative thereof and between 100 mg and 1000 mg of glycine, said glycine derivative or a pharmaceutically acceptable salt thereof.

9. The method according to claim 1, wherein the active agent includes a ratio of methylsulphonylmethane:glucosamine:glycine of 1-3:1-3:1-3.

10. The method according to claim 1, wherein the active agent further includes nicotinamide, or a salt thereof.

11. The method according to claim 1, wherein the active agent further includes vitamin $B_{12}$.

12. The method according to claim 1, wherein the composition further includes a pharmaceutically acceptable diluent, carrier or excipient.

13. The method according to claim 1, wherein the inflammatory skin disorder is selected from psoriasis, sunburn, reaction to insect bites and stings, eczema, pompholyx, pterygium, seborrheic dermatitis and solar keratosis.

14. The method according to claim 1, wherein the cardiac disorder is hypertension.

* * * * *